United States Patent [19]

Frass et al.

[11] Patent Number: 5,499,625

[45] Date of Patent: Mar. 19, 1996

[54] ESOPHAGEAL-TRACHEAL DOUBLE LUMEN AIRWAY

[75] Inventors: Michael Frass; Reinhard Frenzer, both of Moedling, Austria; Gregor Long, Lake George; John S. Kline, Queensbury; David S. Sheridan, Argyle; E. David Fink, Rexford; Anthony N. Toppses, Ganesvoort, all of N.Y.

[73] Assignee: The Kendall Company, Mansfield, Mass.

[21] Appl. No.: 186,915

[22] Filed: Jan. 27, 1994

[51] Int. Cl.$^6$ ............................................... A61M 16/04
[52] U.S. Cl. .................. 128/207.15; 128/200.26; 128/207.14; 128/911; 128/912
[58] Field of Search ............... 128/200.26, 207.14, 128/207.15, 207.16, 207.17, 911, 912, DIG. 26

[56] References Cited

U.S. PATENT DOCUMENTS

| | | |
|---|---|---|
| 3,788,328 | 1/1974 | Alley et al. . |
| 3,862,635 | 1/1975 | Harautuneian . |
| 3,884,242 | 5/1975 | Bazell et al. . |
| 4,090,518 | 5/1978 | Elam .................. 128/207.15 |
| 4,231,365 | 11/1980 | Scarberry .......... 128/207.15 |
| 4,233,984 | 11/1980 | Walling ............. 128/207.14 |
| 4,327,720 | 5/1982 | Bronson et al. ........ 128/911 |
| 4,327,721 | 5/1982 | Goldin et al. ...... 128/207.15 |
| 4,444,185 | 4/1984 | Shugar .............. 128/200.26 |
| 4,523,920 | 6/1985 | Russo .................. 604/93 |
| 4,530,354 | 7/1985 | Froilan ............. 128/207.17 |
| 4,584,998 | 4/1986 | McGrail ............ 128/207.15 |
| 4,588,399 | 5/1986 | Nebergall et al. ... 128/207.15 |
| 4,688,568 | 8/1987 | Frass et al. . |
| 4,819,664 | 4/1989 | Nazari ............... 128/207.15 |
| 4,976,261 | 12/1990 | Gluck et al. ....... 128/207.15 |
| 5,203,777 | 4/1993 | Lee ...................... 604/280 |
| 5,259,371 | 11/1993 | Tonrey ............... 128/200.26 |
| 5,285,778 | 2/1994 | Mackin .............. 128/200.26 |
| 5,311,864 | 5/1994 | Huerta ............... 128/207.17 |
| 5,315,992 | 5/1994 | Dalton ............... 128/207.14 |

FOREIGN PATENT DOCUMENTS

| | | | |
|---|---|---|---|
| 2098485 | 11/1982 | United Kingdom | 128/207.15 |
| 2171017 | 8/1986 | United Kingdom | 128/207.15 |

*Primary Examiner*—Edgar S. Burr
*Assistant Examiner*—William J. Deane, Jr.
*Attorney, Agent, or Firm*—Burns, Doane, Swecker & Mathis

[57] ABSTRACT

An airway for both sole esophageal obturator ventilation and for combined endotracheal and esophageal obturator ventilation of a patient. The airway has two lumens one of which has an open distal end and the other of which has a closed distal end. The airway further has an inflatable distal cuff and an inflatable pharyngeal cuff. Communicating with the lumen having the closed distal end is at least one air outlet located in the airway wall between the two inflatable cuffs. To determine the position and orientation of the airway within a patient, the airway is provided with an X-ray opaque stripe that preferably axially extends in the wall, but is interrupted by at least one air outlet between the inflatable cuffs. An X-ray opaque shaft may also be present between the inflatable cuffs and is preferably attached to the wall. The airway may also be provided with monitoring lumens and deflector means in communication with the lumen that has the open distal end. To facilitate fiber optic examination of the patient, some of the air outlets adjacent the pharyngeal cuff may be larger than the other air outlets.

23 Claims, 2 Drawing Sheets

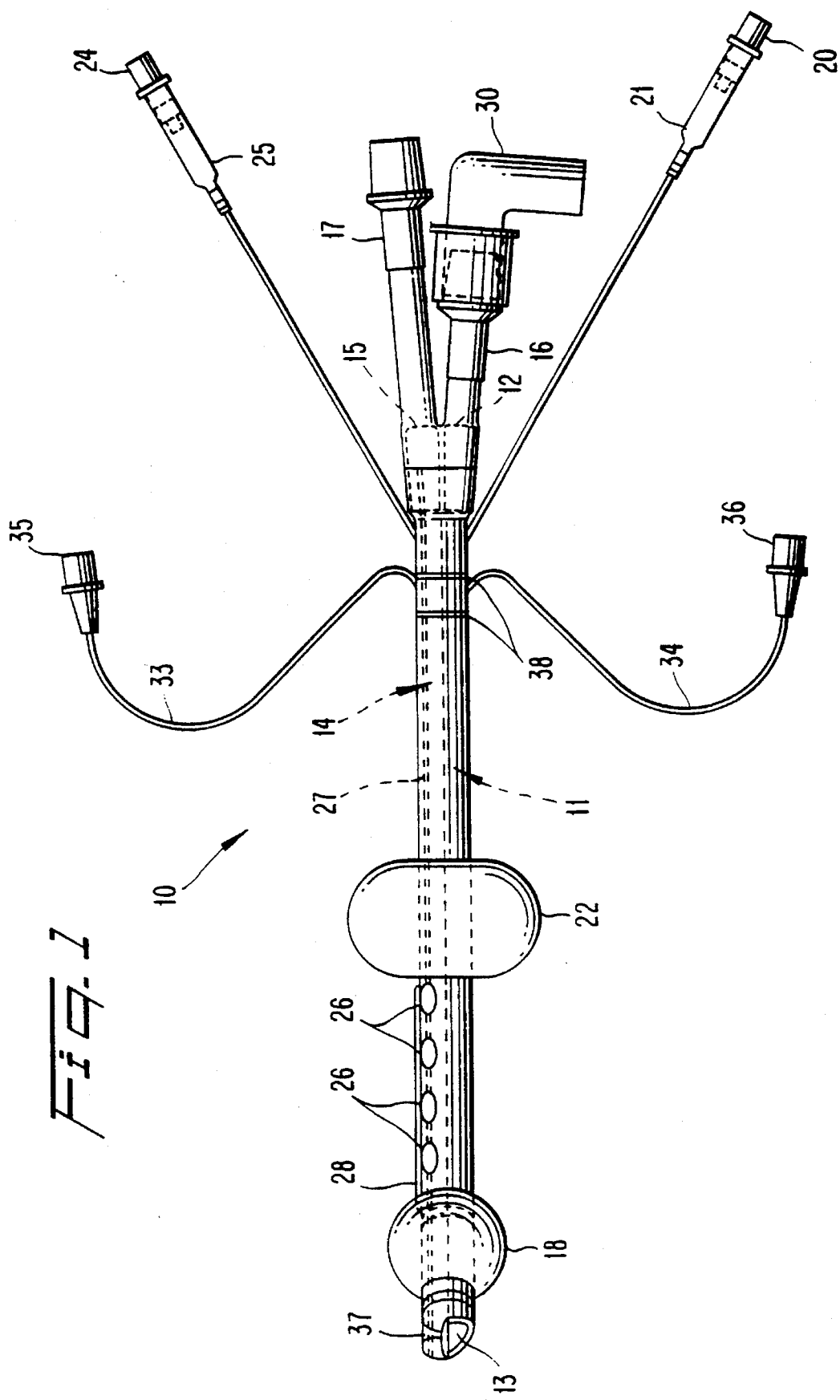

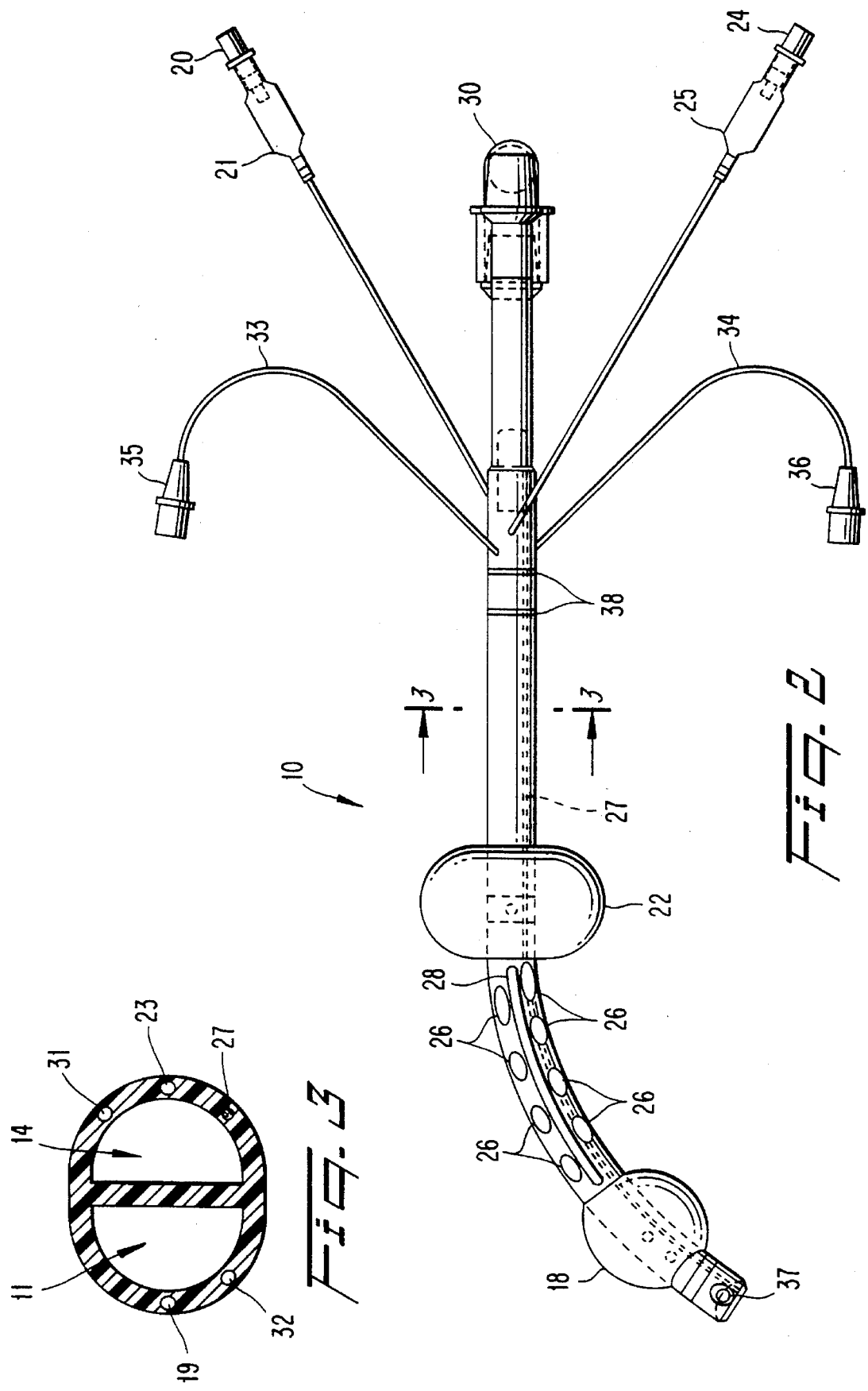

5,499,625

ESOPHAGEAL-TRACHEAL DOUBLE LUMEN AIRWAY

BACKGROUND OF THE INVENTION

1. Field of the Invention

The present invention relates to an airway for sole esophageal obturator or endotracheal and esophageal-obturator ventilation. The airway of the present invention particularly relates to an airway that is used in an emergency situation and whose position and orientation can subsequently be accurately determined by X-ray, ultrasonographic or fluoroscopic examination.

2. Description of the Related Art

Airways have been developed for use in emergency resuscitation so that the insertion of the airway by first-aid personnel can be performed. For instance, a single-lumen airway for insertion into the esophagus that is sealed to the external environment by a face mask is known, e.g., by Don Michael T. A., Lambert E. H., Mehran A.; Lancet p. 1329, 1968. During ventilation air is guided from the lumen of the airway through the air-outlets to the patient. However, the sealing of the airway against the surrounding air is problematic as one has to press the face mask to the face of the patient to obtain adequate an effective seal thereby usually demanding an assistant.

A twin-lumen airway is described in AT-PS No. 376,128. This airway can be inserted into the trachea or into the esophagus by choice. In the first case, the air passes from the one lumen directly into the trachea, while in the second case the air passes from the other lumen through the air outlets. Also with this airway a face mask is recommended.

According to DE-OS No. 21 20 164, an airway is provided which shows two parallel tubes. One tube is inserted into the esophagus and may be sealed by a cuff. This tube does not conduct air but is used to withdraw gastric fluid by suction. Ventilation is carried out through the second tube which ends in the cavum pharynges. For sealing purposes, a further cuff may be provided replacing a mask by sealing the cavum pharynges directly. However this airway must not be inserted into the trachea or esophagus by choice. If this airway is inserted into the trachea, ventilation is impossible.

Other emergency airways are described in U.S. Pat. Nos. 4,231,365, 4,334,534 and 4,688,568. In U.S. Pat. No. 4,231,365, there is illustrated an emergency resuscitation apparatus including an endotracheal tube having a tracheal obturator and a second expandable cuff for sealing against the pharyngeal tissues to provide an alternate sealing for respiratory fluids if the blind intubation is not successful. A laryngeal tube passes through the pharyngeal obturator for alternatively introducing respiratory fluids into the lungs through the larynx. The endotracheal tube may also be used as an esophageal obturator and inserted without the intubating guide means. To support the tubes and ensure intubation to the correct depth, a face shield is provided.

U.S. Pat. No. 4,334,534 describes an emergency airway tube for use in resuscitation of non-breathing patients by inserting the tube through the mouth until it randomly lodges either in the trachea or the esophagus. The tube has an outer tube, an inner tube which runs along and within the bore of the outer tube, and an air passageway for inflating an inflatable cuff located at the distal end of the outer tube which enters the trachea or esophagus. The end of the inner tube has a pneumatic seal for forming an airtight fit within an adjacent distal end of the outer tube. The outer tube has a cluster of side air ports in its wall located generally midway between the ends of the tube. If the tip of the tube engages the trachea on insertion, the cuff is inflated and the inner tube will be the air passageway to ventilate the patient. If the tip of the tube engages the esophagus, the cuff will seal off the stomach. The outer tube will be the air passageway to ventilate the lungs by way of the side air ports in the outer tube wall. A face mask is placed over the face of the patient to stop air leakage while the patient is being ventilated via the air ports.

U.S. Pat. No. 4,688,568 discloses an airway for sole esophageal obturator or endotracheal and esophageal-obturator ventilation by choice. The airway has an inflatable distal cuff and air outlets in its wall in the area of the pharynx. The airway also has an inflatable pharyngeal cuff that surrounds the wall of the airway above the air outlets in that area and which, when the airway is inserted, is situated between the soft palate and the boundary between the base of the tongue and the back of the tongue.

Although known emergency airways have been used to successfully resuscitate patients, a problem can arise when the patient is further treated by personnel different from those who originally inserted the airway. In particular, it is sometimes difficult to determine the precise position and orientation of the airway within the patient which may be crucial before the patient can be further treated. Furthermore, it is undesirable to remove and reposition the airway or to use a new airway in view of time and possible additional danger to the patient, particularly in instances of spinal or facial trauma.

While the art has described an X-ray marking line in conventional endotracheal tubes, such as in U.S. Pat. No. 4,150,676, there is still a need for an efficient and effective way to determine the precise location of a double lumen airway.

OBJECTS AND SUMMARY OF THE INVENTION

It is accordingly one object of the present invention to provide an airway whose position within a patient can be quickly and precisely determined.

It is a further object of the present invention to provide a double lumen airway wherein the flow through either lumen can be monitored.

It is a still further object of the present invention to provide an airway wherein a location determining or treatment device can be passed through the airway to a position outside the airway within the patient without disturbing the position of the airway within the patient.

It is a yet further object of the present invention to provide means for deflecting any fluid emitted from a lumen having an open distal end.

It is a yet further object of the present invention to provide connectors that resist kinking.

In one aspect, the present invention relates to an airway for both sole esophageal obturator ventilation and for combined endotracheal and esophageal obturator ventilation of a patient, selectively, comprising:

tube means having a proximal end and a distal end, said distal end being insertable into an esophagus or into a trachea randomly, said tube means defining two lumens extending axially and each having a proximal end and a distal end, both of said lumens being open at the proximal end, the distal end of one of said lumens being open and the distal end of the other of said lumens being closed, said tube means further defining at least one air outlet communicating with said lumen having said closed distal end and which is locatable in a patient's pharyngeal area;

an inflatable distal cuff on said tube means located adjacent the distal end of said tube means;

inflation conduit means connected to said inflatable distal cuff for allowing selective inflation of said inflatable distal cuff;

an inflatable pharyngeal cuff on said tube means located between said at least one air outlet and said proximal end of said tube means, said pharyngeal cuff being sized and located with respect to said tube means such that when inflated, it is situated within the boundaries of the oropharynx of a patient;

inflation conduit means connected to said inflatable pharyngeal cuff for allowing selective inflation of said pharyngeal cuff; and an X-ray opaque stripe extending along the tube means, said stripe being present at least between the inflatable pharyngeal cuff and the inflatable distal cuff and being interrupted by at least one air outlet.

BRIEF DESCRIPTION OF THE DRAWINGS

The present invention can be further understood with reference to the following description in conjunction with the appended drawings, wherein like elements are provided with the same reference numerals. In the drawings:

FIG. 1 is a bottom view of an illustrative embodiment of the present invention.

FIG. 2 is the side view of the illustrative embodiment of the present invention illustrated in FIG. 1.

FIG. 3 is an transverse cross-sectional taken along the line A—A of FIG. 2.

DESCRIPTION OF THE PREFERRED EMBODIMENTS

With reference to the illustrative embodiment shown in the drawings, the airway generally indicated at 10 is a twin-lumen airway suitable for ventilation in the endotracheal position or esophageal-obturator position. The airway has one continuous lumen 11 with an open proximal end 12 and open distal end 13 and a second lumen 14 which has an open proximal end 15 and is sealed at the distal end. The airway is preferably composed of a thermoplastic material such as polyvinyl chloride or a non-thermoplastic material such as silicone and can be prepared by extrusion and melt forming as is well known in the art. The lumens 11 and 14 are in parallel or coaxial to one another and are provided with connectors 16 and 17, respectively that can be used to connect the airway to conventional ventilation equipment. The connectors can be prepared of conventional material, such as polyvinyl chloride or polyurethane, and can be of different length, as illustrated, to enable ready recognition between the connections to the two lumens. To this end, it is also preferable that the connectors comprise different colors. In addition, the connectors are preferably constructed to reduce the tendency of kinking. This can be achieved by various techniques such as thickening the walls of the connectors, selecting a material of construction with higher flexural strength or by reinforcing the connector wall.

As an integral or additional piece, the coupling communicating with lumen 11 having open distal end 13 is provided with a deflector 30 to protect attending medical personnel from inadvertent fluid discharge. The deflector may comprise an elbow having an angle of from about 30° to 90° so that fluid will be deflected away from attending medical personnel. If desired, the deflector can be in the form of a fitting so that ejected fluids can be diverted to a container via an appropriate tubing. The deflector may also be constructed so as to be rotatable in order to make positioning easier.

Towards the distal end, the wall of the airway is surrounded by an inflatable distal cuff 18 well known in the art. For instance, the cuff can be composed of a silicone or thermoplastic material such as polyvinyl chloride which extends from about 1 to about 10 centimeters along the airway wall. The cuff is adhered to the wall of the airway by a conventional adhesive such as a cyclohexanone/polyvinyl chloride mixture. The edge of the cuff is typically located from about 0.5 to about 5 centimeters from the tip of the airway. Cuff 18 is inflated and deflated via conduit 19 which preferably is formed in the wall of the airway, extends through a flexible tubing, and ends in connector 20. A pilot balloon 21 can be present to indicate the inflation status of cuff 18. Additional information relating to distal cuffs may be found in the aforementioned U.S. patents, the contents of which are incorporated by reference.

The airway also has an inflatable pharyngeal cuff 22 which is designed so as to be situated within the boundaries of the oropharynx of a patient. The pharyngeal cuff, in the same manner as the cuff 18, surrounds the wall of the airway, communicates with conduit 23 which is again preferably formed in the wall of the airway, extends through a flexible tubing and ends in connector 24. A pilot balloon 25 can be present to indicate the inflation status of pharyngeal cuff 22. The pharyngeal cuff may be composed of latex or an elastic material such as polyvinyl chloride and can be adhered to the wall of the airway by a conventional adhesive such as a cyanoacrylate adhesive. The shape and dimensions of the pharyngeal cuff may be those described in U.S. Pat. No. 4,688,568, the contents of which have been incorporated by reference.

The airway is provided with at least one and preferably a plurality of air outlets 26 communicating with lumen 14. The air outlets are located between inflatable distal cuff 18 and inflatable pharyngeal cuff 22 and are designed to be located in the pharyngeal area of a patient. When a plurality of outlets are present, they are preferably arranged in a plurality of rows circumferentially spaced in the tube means with each row formed of a plurality of air outlets axially spaced along the tube means. As illustrated in FIG. 2, this portion of the airway is typically curved to approximate the natural curvature of the pharynx. In order to permit verification of the placement of the airway by means of a fiberoptic scope shaft or possible treatment (e.g., suctioning of tracheal secretions while in the esophageal position) of the patient in the vicinity of the air outlets, the air outlets adjacent to the pharyngeal cuff can be made larger than the other air outlets. For example, the cross-sectional area of the outlets adjacent the pharyngeal cuff can be from about 100 to about 500% larger than the cross-sectional area of the other air outlets.

In order for medical personnel to ascertain the placement and orientation of the airway and locations of the inflatable cuffs, the airway wall is provided with an X-ray opaque stripe 27 composed of a well known material such as barium sulfate. The stripe may be from about 0.1 to about 5 millimeters wide and is preferably incorporated into the wall of the airway. Such incorporation can be achieved by injecting a blend of a thermoplastic material, such as polyvinyl chloride, and the barium sulfate into the wall of the airway as the airway is extruded. The X-ray opaque stripe is present at least between the inflatable pharyngeal cuff and the inflatable distal cuff, but is interrupted by at least one air outlet that can be formed by conventional techniques such as by hot or cold punching, drilling or by using a laser. In this way, medical personnel can readily determine the placement of the airway upon X-ray, ultrasonography or fluoroscopic examination. Typically, the X-ray opaque stripe is present along the entire airway wall except where interrupted by the at least one air outlet. When a plurality of air outlets are provided, the X-ray opaque stripe can be interrupted by more than one air outlet. For instance, as illustrated in FIG. 2, when the air outlets are arranged in a plurality of rows, the air outlets of one row may each interrupt the X-ray opaque stripe thereby readily permitting determination of the placement of the airway in the patient by X-ray, ultrasonographic or fluoroscopic examination. If desired one or more additional stripes (not shown) may be present.

The airway may also be provided with an X-ray opaque shaft 28 that is located between the inflatable distal cuff and the inflatable pharyngeal cuff. The X-ray opaque shaft is flexible and is composed of a known material such as a thermoplastic material exemplified by polyvinyl chloride which contains barium sulfate. The shaft is typically cylindrical in shape with a diameter of from about 1 to about 5 millimeters and a length of from about 1 to about 15 centimeters. The shaft is preferably attached to the wall of the airway between two rows of air outlets. In this arrangement, the X-ray opaque shaft can serve the additional function of helping to keep the air outlets from being blocked by mucosa or other parts of the body, as well as facilitating determination of the placement and orientation of the airway in the patient by X-rays, ultrasonography or fluoroscopy. If desired, one or more additional X-ray opaque shafts (not shown) may be present.

In order to confirm placement of the airway in the trachea or esophagus with a capnograph, the illustrated airway is provided with monitoring lumens 31 and 32 which are preferably located in the tube wall and communicate with the two lumens 11, 14 of the airway at their distal ends. The monitoring lumens communicate with flexible tubings 33 and 34 which can be provided with standard connectors 35 and 36. Medication may also be administered through either monitoring lumen.

The open distal end 13 of lumen 11 may form an obtuse angle with respect to the wall of the airway, as illustrated in FIG. 1, so as to help maintain the opening free of mucosa or other parts of the body. To achieve this form, the tip of the airway can be melt processed into the desired shape. Alternatively, a cap can be fitted to the open distal end as illustrated in aforementioned U.S. Pat. No. 4,688,568. To help maintain an open passage to lumen 11, a further opening 37 can be formed in the wall, such as by using a punch, which opening communicates with the lumen 11 in the vicinity of open distal end 13.

The overall size of the airway and the location and sizes of the inflatable cuffs can be selected in a manner known to those skilled in the art. For instance, if the airway is designed for a young patient, the relative size of the airway and the inflatable cuffs will be respectively smaller than an airway designed for adult use. As is also known in the art, the airway may be provided with indicator markings 38 to indicate the depth of insertion of the airway in the patient.

To use the airway of the present invention, the patient is preferably placed in a supine position, the tongue and lower jaw are lifted and the airway is inserted so that the curve of the airway is in the same direction as the natural curvature of the pharynx. The approximate depth of insertion can be determined by aligning the teeth of the patient with indicator markings 38. With the airway in position, the pharyngeal cuff 22 is inflated to an appropriate degree, for instance by using a syringe to inject about 100 ml of air in an airway designed for adult use. The pilot balloon 25 will indicate the inflated status of the pharyngeal cuff. The distal cuff 18 may be then inflated to an appropriate degree, for instance by using a syringe to inject about 15 ml of air. The pilot balloon 21 will indicate the inflated status of the distal cuff.

With both cuffs inflated, ventilation with conventional means can be initiated through either lumen. For instance, ventilation can be initiated through lumen 14 communicating with air outlets 26. If auscultation of breath sounds is positive and auscultation of gastric insufflation is negative, which may be confirmed by observing chest expansion, ventilation can be continued. In this situation, lumen 11 may be used for the removal of gastric fluids. Should such fluids be ejected from the patient, deflector 30 will direct the fluids away from attending personnel.

If, on the other hand, auscultation of breath sounds is negative and gastric insufflation is positive, ventilation should be immediately switched to lumen 11. Successful ventilation can again be confirmed by auscultation of breath sounds and absence of gastric insufflation.

To determine the precise location and orientation of the airway in the patient, an X-ray, ultrasonography or fluoroscopic examination can be conducted. The X-ray opaque stripe(s) interrupted by air outlet(s) and the X-ray opaque shaft, if present, can be observed from the examination. If an X-ray opaque adhesive is used for attachment of the cuff(s), the location of the cuff(s) can also be readily determined. A fiber optic examination of the patient may also be conducted by passing a fiberoptic scope through lumen 14 and through an air outlet, particularly a larger sized outlet adjacent the pharyngeal cuff. In addition, monitoring of the lumens 11 and 14 can be conducted via the monitoring lumens and the use of a capnograph. If warranted, the airway permits treatment of the patient through lumen 14 and one of the air outlets or through lumen 11 and distal end 13 or through one of the monitoring lumens.

While certain preferred features of the invention have been shown by way of illustration and discussion, many modifications will occur to those of ordinary skill in the art. It is to be understood therefor that the following claims are intended to cover all such modifications and changes as fall within the spirit and scope of the invention.

We claim:

1. An airway for both sole esophageal obturator ventilation and for combined endotracheal and esophageal obturator ventilation of a patient, selectively, comprising:

a tube having an exterior surface, a proximal end and a distal end, said distal end being insertable into an esophagus or into a trachea randomly, said tube comprising two lumens extending axially and each having a proximal end and a distal end, both of said lumens being open at the proximal end, the distal end of one of said lumens being open and the distal end of the other of said lumens being closed, said tube further comprising at least one air outlet communicating with said lumen having said closed distal end wherein said at least one air outlet is locatable in a patient's pharyngeal area;

an inflatable distal cuff on said tube located adjacent the distal end of said tube;

an inflation conduit connected to said inflatable distal cuff for allowing selective inflation of said inflatable distal cuff;

an inflatable pharyngeal cuff on said tube located between said at least one air outlet and said proximal end of said tube, said pharyngeal cuff being sized and located with respect to said tube such that when inflated, said pharyngeal cuff is situated within the boundaries of the oropharynx of a patient;

an inflation conduit connected to said inflatable pharyngeal cuff for allowing selective inflation of said pharyngeal cuff;

an X-ray opaque stripe extending along the tube, said stripe being present at least between the inflatable pharyngeal cuff and the inflatable distal cuff and being interrupted by at least one air outlet; and an X-ray opaque shaft separate from the X-ray opaque stripe, said X-ray opaque shaft being attached to the exterior surface of the tube between the inflatable pharyngeal cuff and the inflatable distal cuff and being constructed to maintain said at least one air outlet interrupting said X-ray opaque stripe free from blockage when the airway is positioned in the patient.

2. The airway of claim 1 wherein said X-ray opaque stripe is incorporated into a wall of said tube and extends from the proximal end to the distal end.

3. The airway of claim 1 wherein said tube has a plurality of air outlets communicating with said lumen having said closed distal end and said X-ray opaque stripe is interrupted by a plurality of air outlets.

4. The airway of claim 3 wherein the plurality of air outlets are arranged in a plurality of rows circumferentially spaced on the tube and the X-ray stripe is interrupted by the air outlets in one of said rows.

5. The airway of claim 1 wherein said tube has a plurality of air outlets arranged in a plurality of rows circumferentially spaced on the tube and said X-ray opaque shaft is attached to the exterior surface of the tube and is located between two of said rows of air outlets.

6. The airway of claim 1 wherein said X-ray opaque shaft is a flexible cylinder having a diameter of from about 1 to about 5 millimeters.

7. The airway of claim 1 wherein at least one of the inflatable distal cuff and the inflatable pharyngeal cuff is attached to the tube with X-ray opaque adhesive.

8. The airway of claim 1 wherein the airway further comprises two monitoring lumens, one monitoring lumen being in communication with each of the two lumens of the tube.

9. The airway of claim 8 wherein the monitoring lumens communicate with the lumens of the tube at positions in the vicinity of the distal ends of the lumens.

10. The airway of claim 4 wherein each row of air outlets includes an air outlet located adjacent the inflatable pharyngeal cuff, said air outlet in each row that is located adjacent the inflatable pharyngeal cuff being larger than the other air outlets of the row.

11. The airway of claim 1 wherein the proximal end of the lumen having the open distal end is connected to a deflector for deflecting fluid exiting the proximal end of the lumen.

12. The airway of claim 11 wherein said deflector is an elbow deflector having an angle of from about 30° to about 90°.

13. The airway of claim 12 wherein the elbow is rotatable.

14. The airway of claim 1 wherein the inflation conduit that is connected to the inflatable distal cuff includes a pilot balloon for indicating an inflation condition of the inflatable distal cuff.

15. The airway of claim 1 wherein the inflation conduit connected to the inflatable pharyngeal cuff includes a pilot balloon for indicating an inflation condition of the inflatable pharyngeal cuff.

16. The airway of claim 1 wherein the airway further comprises a first connector and a second connector, said first connector being in communication with the proximal end of one of the lumens of the tube and the second connector being in communication with the other lumen of the tube.

17. The airway of claim 16 wherein the length of the first connector is different from the length of the second connector.

18. The airway of claim 17 wherein the first connector comprises a different color than the second connector.

19. The airway of claim 16 wherein the first and second connectors are constructed to resist kinking.

20. The airway of claim 1 wherein the two lumens of the tube are parallel.

21. The airway of claim 1 wherein said open distal end of the lumen of the tube forms an obtuse angle relative to a wall of the tube.

22. The airway of claim 21 wherein said lumen having an open distal end, communicates with the exterior of the tube through a further opening, said further opening being located near the distal end of the tube.

23. The airway of claim 1 wherein the airway further comprises at least one position indicating marking on the tube.

\* \* \* \* \*